United States Patent [19]

Burns

[11] Patent Number: 5,192,275
[45] Date of Patent: Mar. 9, 1993

[54] IV INFUSION OR BLOOD COLLECTION GUARD ASSEMBLY

[75] Inventor: James A. Burns, Elizabeth, N.J.

[73] Assignee: Becton, Dickinson and Company, Franklin Lakes, N.J.

[21] Appl. No.: 762,535

[22] Filed: Sep. 18, 1991

[51] Int. Cl.$^5$ .................. A61M 5/00; A61M 5/32
[52] U.S. Cl. .................. 604/263; 604/177
[58] Field of Search ............ 604/162, 164, 165, 167, 604/171, 177, 178, 192, 198, 263, 110

[56] References Cited

U.S. PATENT DOCUMENTS

| | | | |
|---|---|---|---|
| 3,262,449 | 7/1966 | Pannier, Jr. et al. | 604/162 X |
| 3,714,945 | 2/1973 | Stanley . | |
| 3,890,972 | 6/1975 | Standley et al. | 604/110 |
| 4,170,993 | 10/1979 | Alvarez . | |
| 4,417,887 | 11/1983 | Koshi | 604/162 |
| 4,676,783 | 6/1987 | Jagger et al. . | |
| 4,781,692 | 11/1988 | Jagger et al. . | |
| 4,832,696 | 5/1989 | Luther et al. | 604/164 |
| 4,846,805 | 7/1989 | Sitar | 604/165 |
| 4,850,961 | 7/1989 | Wanderer et al. | 604/53 |
| 4,863,434 | 9/1989 | Bayless | 604/198 |
| 4,888,001 | 12/1989 | Schoenberg . | |
| 4,917,669 | 4/1990 | Bonaldo | 604/164 |
| 4,927,415 | 5/1990 | Brodsky | 604/164 |
| 4,929,241 | 5/1990 | Kulli | 604/263 |
| 4,935,012 | 6/1990 | Magre et al. | 604/192 |
| 4,941,881 | 7/1990 | Masters et al. . | |
| 4,943,283 | 7/1990 | Hogan . | |
| 4,946,446 | 8/1990 | Vadher | 604/198 |
| 4,950,252 | 8/1990 | Luther et al. | 604/198 |
| 5,000,740 | 3/1991 | Ducharme et al. | 604/162 |
| 5,019,049 | 5/1991 | Haining | 604/165 |
| 5,030,212 | 7/1991 | Rose | 604/263 |
| 5,061,250 | 10/1991 | Shields | 604/198 |
| 5,088,982 | 2/1992 | Ryan | 604/110 |
| 5,098,389 | 3/1992 | Cappucci | 604/158 |
| 5,098,403 | 3/1992 | Sampson | 604/198 |
| 5,108,376 | 4/1992 | Bonaldo | 604/171 |
| 5,112,311 | 5/1992 | Utterberg et al. | 604/177 |
| 5,120,320 | 6/1992 | Fayngold | 604/177 |
| 5,147,319 | 9/1992 | Ishikawa et al. | 604/174 |

FOREIGN PATENT DOCUMENTS 0409057 1/1991 European Pat. Off. ............ 604/263

Primary Examiner—C. Fred Rosenbaum
Assistant Examiner—Adam J. Cermak
Attorney, Agent, or Firm—Alan W. Fiedler; Nanette S. Thomas

[57] ABSTRACT

An intravenous infusion set and/or blood collection assembly includes a feature for covering the used needle. The cover is slidably disposed on the assembly and is adapted to be slid relative to the assembly to cover the used needle. The cover is locked in a fully extended position over the used needle so that the assembly is ready for subsequent disposal.

19 Claims, 6 Drawing Sheets

IV INFUSION OR BLOOD COLLECTION GUARD ASSEMBLY

BACKGROUND OF THE INVENTION

1. Field of the Invention

This invention relates to an apparatus for collecting blood or other body fluids, and more particularly to intravenous (IV) infusion sets, and in particular to an IV infusion set with a protective needle cover.

2. Description of Related Art

A conventional IV infusion or blood collection assembly includes an elongated small gauge plastic flexible tubing material having at one end thereof a disposable needle and a body for holding the needle. Usually, the needle body is adhered to the one end of the flexible tube by friction. The needle body includes wings extending on either side for the phlebotomist or user to grasp and hold the needle body for inserting the needle into a patient. Such assemblies may be used for infusing medication into a patient or for collecting blood from a patient. Generally, at the end of the flexible tube opposite the needle body is a female luer connection for connecting supplies of fluid to be infused or for connecting some sort of apparatus for collecting blood, as required.

After the needle of the assembly has been withdrawn from a patient, protection of the used needle tip becomes important. With concern about infection, transmission of AIDS, hepatitis and similar diseases of the blood, methods and devices to enclose the used disposable needle have become very important and in great demand. Many developments have taken place for providing some sort of covering for the used disposable needle, once it is removed from the patient. These structures usually involve some sort of shield arrangement which moves in place over the used needle, once it has been removed from the patient.

Needle guards are of three types which either hide the withdrawn needle within a needle carrying hub, require replacement of a separate needle guard or include a sliding shield which can be positioned distally over the used needle. However, most needle guards are cumbersome and interfere with the one handed needle placement procedure as described in U.S. Pat. No. 3,714,945 to Stanley.

All of the proposed structures disclosed in the art are cumbersome, expensive and may interfere with the normal and accepted procedure of one handed needle placement techniques.

With the increased emphasis on the concern about the proper disposal of IV assemblies, a special need exists for an improved assembly that will have an effective mechanism for covering the used needle without interfering with accepted one handed needle placement techniques. The assembly would effectively cover a used needle and substantially prevent the used needle from making contact outside the covering.

Despite the variety of available devices with needle guard covers, there are apparently no devices with effective covers that may easily be used to cover the needle with one hand and not interfere with accepted needle placement techniques.

SUMMARY OF THE INVENTION

The present invention is an IV infusion and/or blood collection assembly comprising a movable cover so as to cover the needle after it has been used. The cover is slidably disposed on the tubing of the assembly and is adapted to be slid relative to the assembly to cover the used needle. The cover includes means for locking it in position covering the needle.

Most desirably, the arrangement is such that the cooperating parts of the cover form a forward use position over the needle. Thus, by simple movement of the cover into a positive position over the used needle, the assembly is ready for subsequent disposal.

In a preferred embodiment of the invention, the IV infusion and/or blood collection assembly comprises an elongated small gauge plastic flexible tubing material having at one end thereof a needle and a needle body for holding the needle. The needle body comprises flexible wings extending on either side. The assembly further comprises a cover which is slidably disposed in a retracted position on the flexible tubing opposite the needle and needle body. The cover comprises a rearward end, a forward end, a top and bottom surface, opposite sides and indentations on opposite sides extending between the top surface and the bottom surface near the rearward end.

Another preferred embodiment of the invention eliminates the flexible wings on the needle body. Instead, the flexible wings are replaced with a modified wing arrangement connected to the outer forward side surface of the housing. Although the wings are preferably rigid, they may be flexible depending on the need or desirability for ease of use.

It is an advantage of this invention that the position covering the needle so as to provide easy containment of the used needle. The cover assembly is therefore easily disposable with the cover locked in place.

Another advantage of the needle cover disclosed herein is that use of the cover does not require any additional steps, procedures or cumbersome mechanisms which would interfere with accepted one handed needle placement techniques.

With the foregoing and additional features in mind, this invention will now be described in more detail, and other benefits and advantages thereof will be apparent from the following detailed description when taken in conjunction with the accompanying drawings.

DETAILED DESCRIPTION

Figure 1:
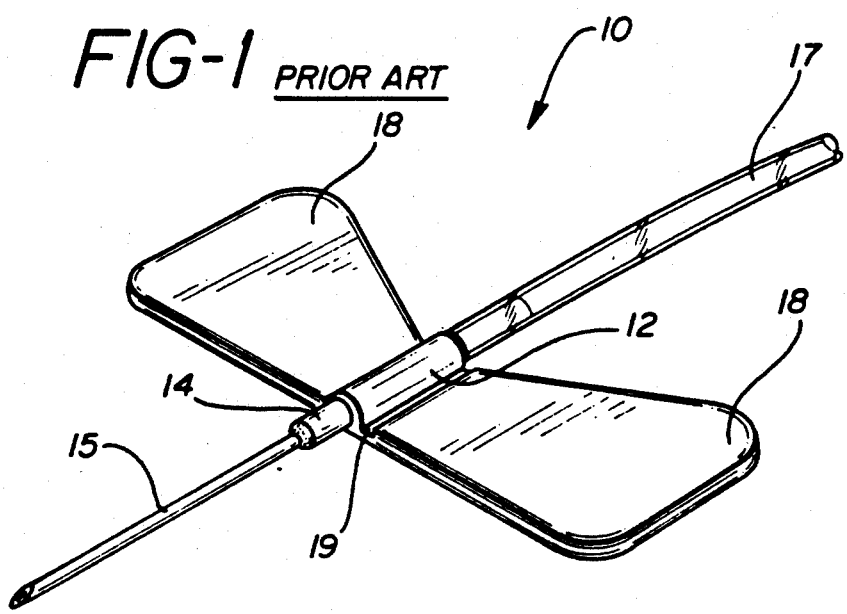
FIG. 1 is a perspective view of a conventional blood infusion set, without the needle cover.

While this invention is satisfied by embodiments in many different forms, there is shown in the drawings and will herein be described in detail preferred embodiments of the invention, with the understanding that the present disclosure is to be considered as exemplary of the principles of the invention and is not intended to limit the invention to the embodiments illustrated. Various other modifications will be apparent to and readily made by those skilled in the art without departing from the scope and spirit of the invention. The scope of the invention will be measured by the appended claims and their equivalents.

Figure 2:
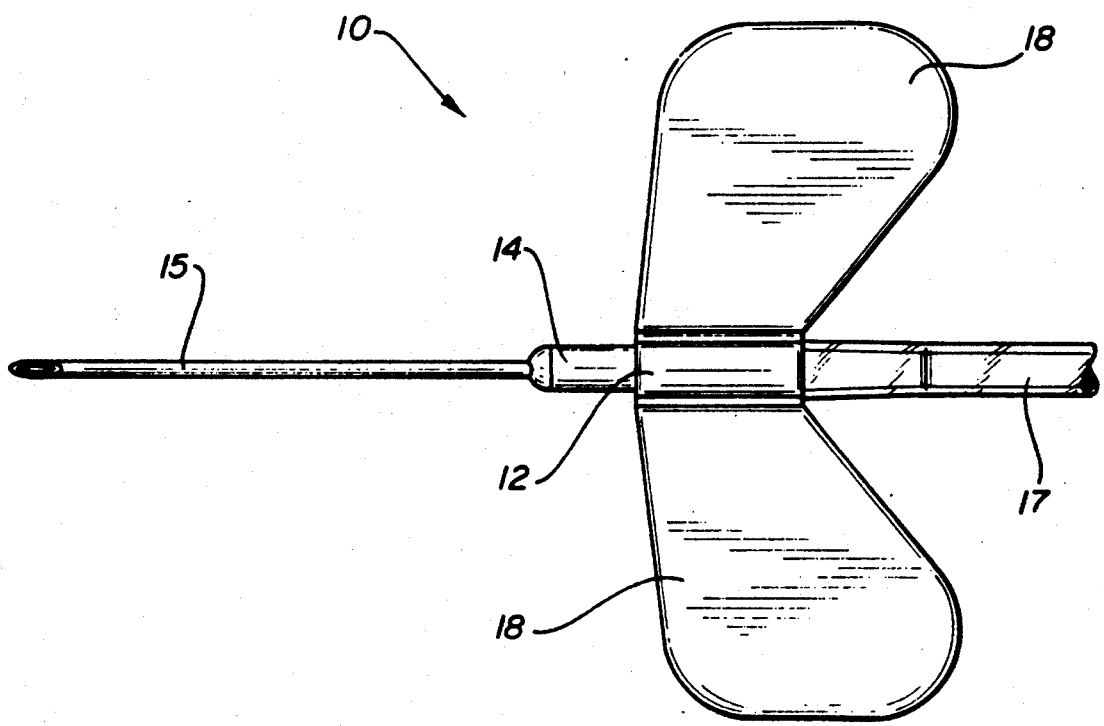
FIG. 2 is a top view of the assembly of FIG. 1.

Referring to the drawings in which like reference characters refer to like parts throughout the several views thereof, FIGS. 1 and 2 show a conventional IV infusion set, 10, or butterfly structure comprising a needle body 12 with a needle hub 14 extending from the forward end of the needle body and a needle 15 embedded in hub 14. Extending from the rearward end of body 12 is flexible tubing 17 which is conventional tubing utilized to allow the user to manipulate the structure of the invention and to connect it subsequently to supplies of infusion liquids, or for the return of collected blood if the arrangement is being used to collect blood.

Infusion set 10 further comprises flexible wings 18 attached to and projected outwardly from needle body 12 Generally, the flexible wings are an integral structure with each wing flexing at a boundary 19.

The invention, as shown in, FIGS. 3-7 includes many components which are substantially identical to the components of FIGS. 1-2. Accordingly, similar components performing similar functions will be numbered identically to those components of FIGS. 1-2, except that a suffix "a" will be used to identify those similar components in FIGS. 3-7.

Figure 3:
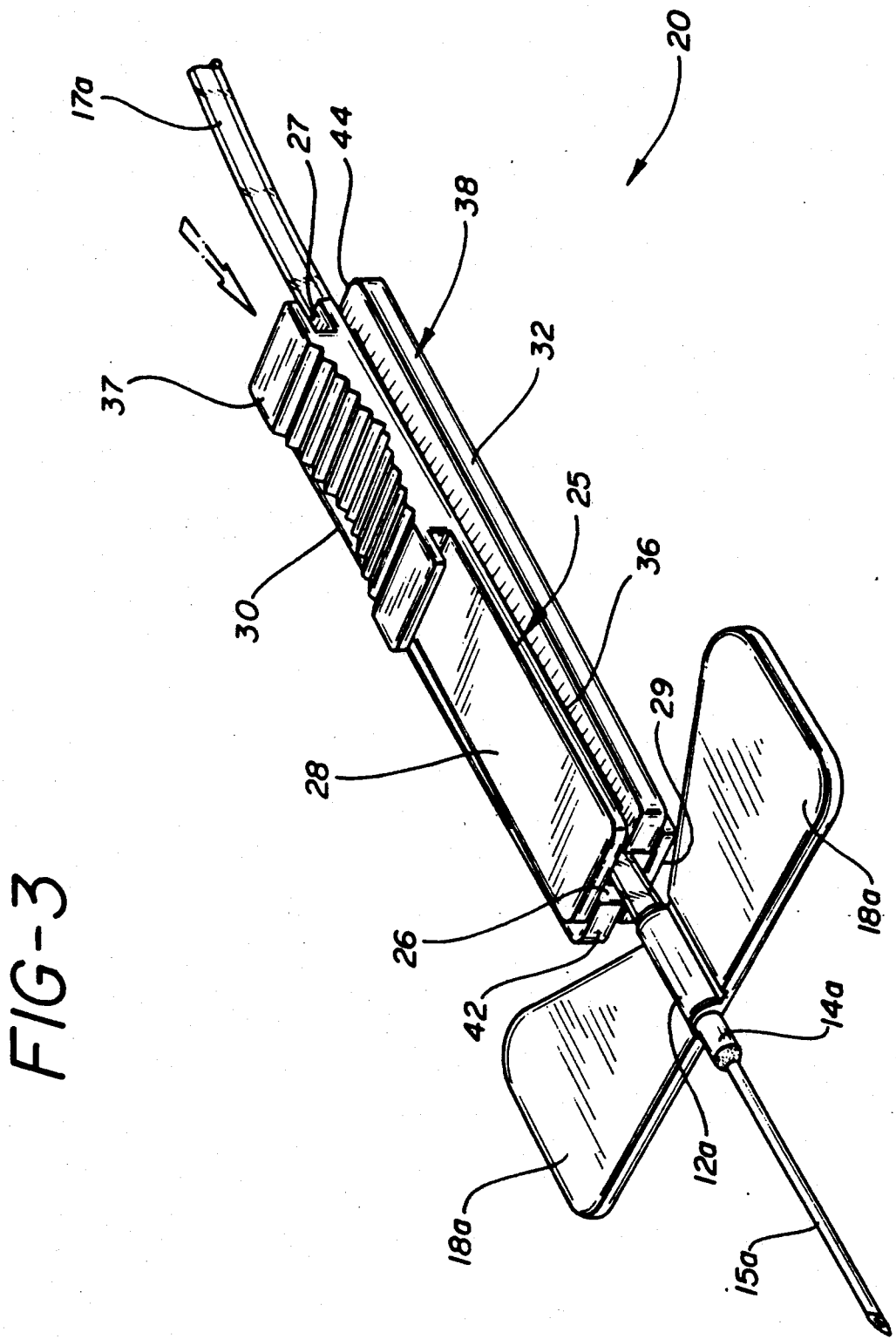
FIG. 3 is a perspective view of a blood infusion set embodying the present invention and having a cover in a retracted position.
Figure 4:
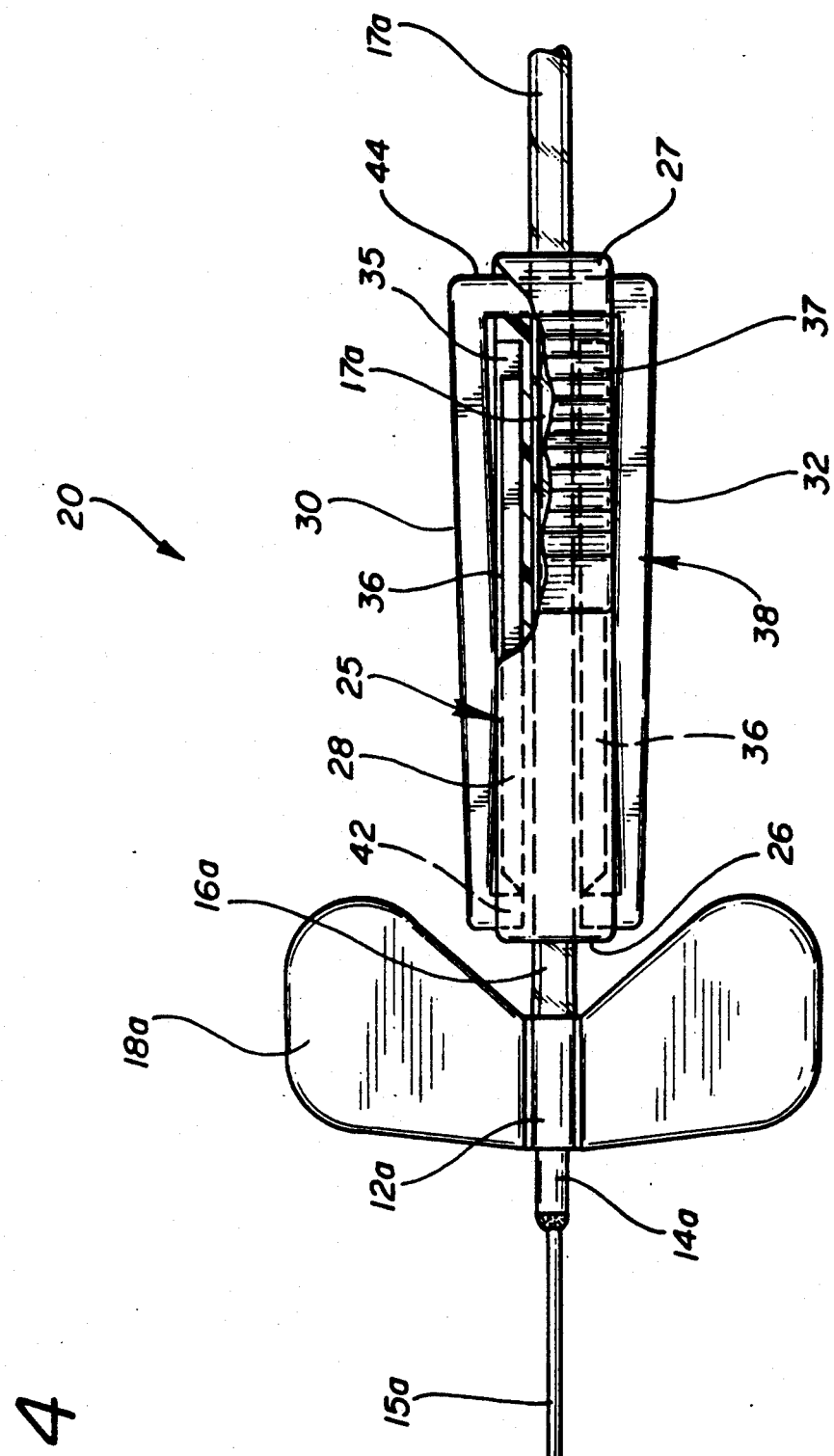
FIG. 4 is a top plan view in partial cross section of the assembly of FIG. 3.
Figure 5:
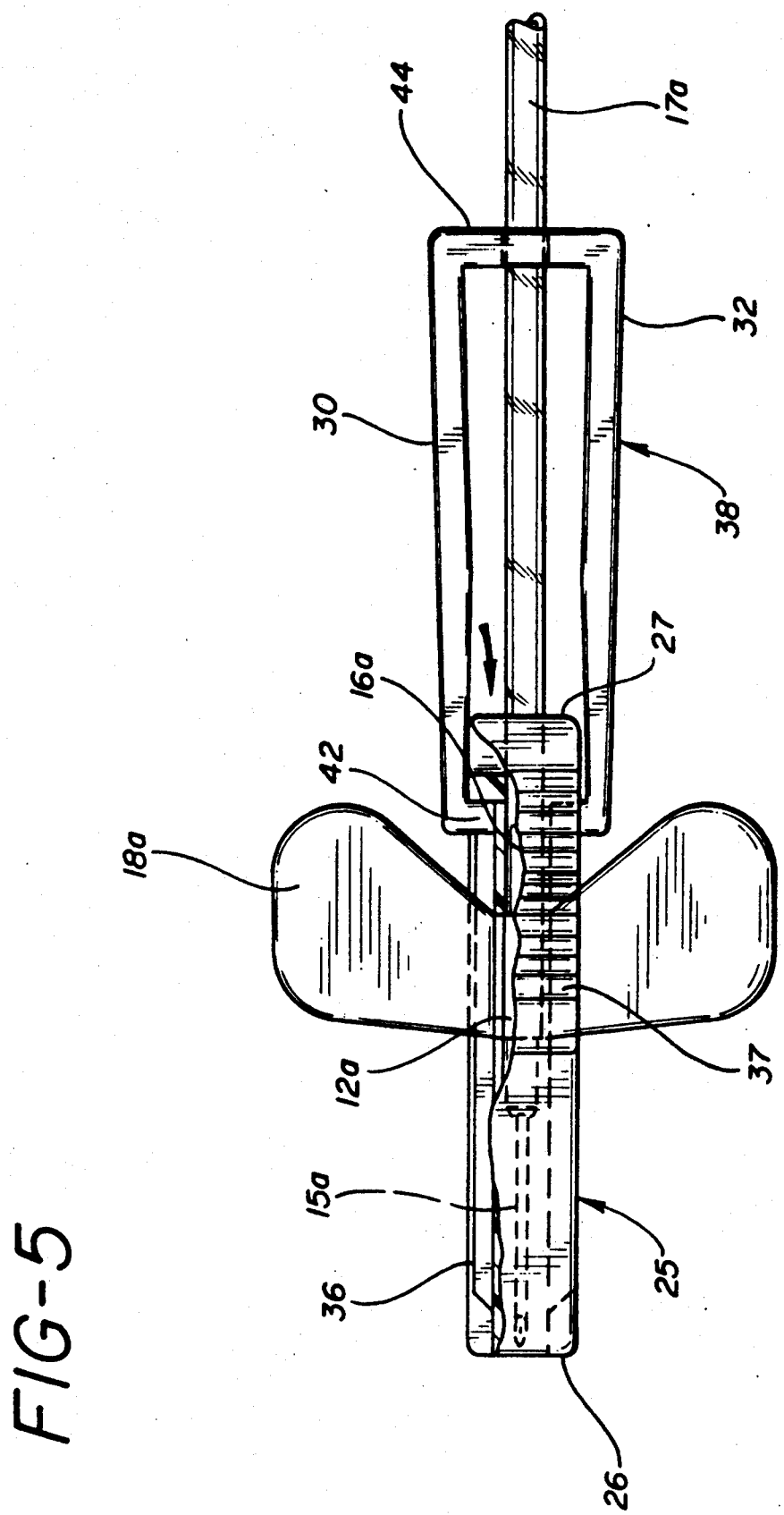
FIG. 5 is a top plan view in partial cross section of FIG. 3 of the assembly with the cover in a forward locked position over the needle.

FIGS. 3-5 show a preferred embodiment of the invention, IV infusion assembly 20 comprising, a needle body 12a, a needle hub 14a extending from the forward end of the needle body and a needle 15a embedded in hub 14a. Extending from the rearward end of body 12a is flexible tubing 17a. Projecting outwardly from and attached to the needle body are flexible wings 18a. The assembly further comprises a cover 25 slidably disposed on tubing 17a. The cover is adapted to be slid past the flexible wings in their flat position to cover the needle after the needle has been used. Although cover 25 is slidably disposed on the tubing, before and during use of the infusion set, the cover is behind wings 18a and thus the wings prevent the cover from interfering with the needle when the IV infusion device is in use.

As shown in FIGS. 3-5, cover 25 preferably comprises a forward end 26 and a rearward end 27, a top side 28, a bottom side 29 and two opposite outer sides 30 and 32. Cover 25 also preferably comprises cavities or indentations 35 near the rearward end of the cover on each outer side. The indentations extend between the top of the cover and the bottom of the cover on each outer side. The cover also comprises at least one longitudinally extending slot 36 extending from the forward end of the cover toward the rearward end, and between the top and bottom sides of the cover. Slot 36 is adapted to surround tubing 17a, receive flexible wings 18a and to allow the cover to be slid past the wings to cover the needle. The cover further comprises a push projection 37 located on the top side of the cover near the rearward end and above the location of the indentations.

Cover 25, in its retracted position as shown in FIGS. 3 and 4, is preferably adapted within a housing 38. Housing 38 preferably comprises an open forward end with inwardly extending biased locking lugs 42 and a closed rearward end 44. The housing surrounds the longitudinally extending slot of the cover and the locking lugs form a barrier at the forward end of the cover to keep it in a retracted position while the assembly is being used.

After the needle is used, the cover is moved to cover the used needle. Forward motion is applied to the push projection with the finger so as to move the cover past the locking lugs of the housing axially forward towards the needle. Locking lugs 42 thereafter engage indentations 35 of the cover when the cover is fully extended over the needle. FIG. 5 shows the cover in a fully extended position covering the needle and that within and adapted through the center of housing 38 is tubing 17a.

Figure 6:
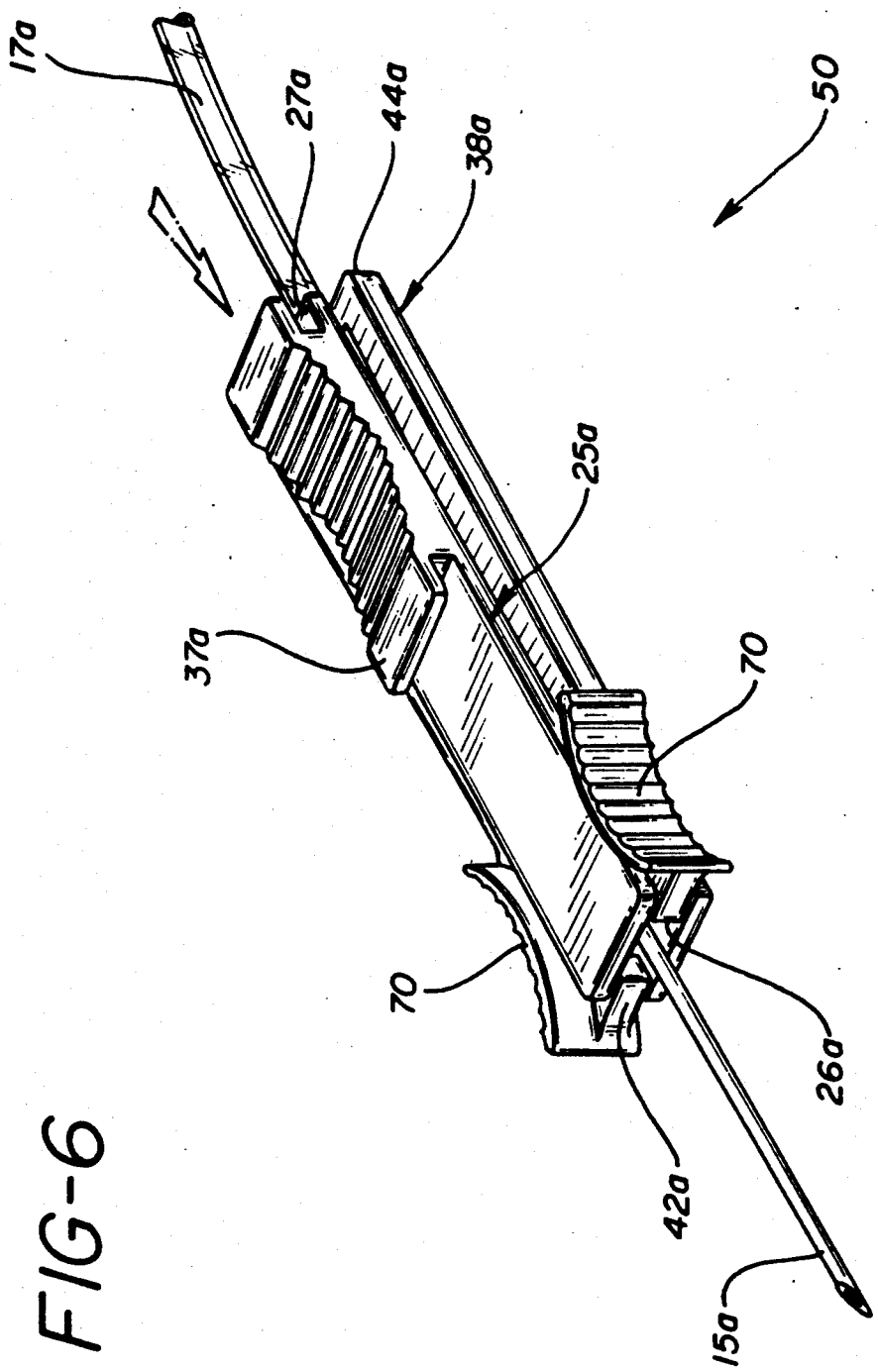
FIG. 6 is a perspective view of a blood infusion set similar to the set of FIG. 3 illustrating an additional embodiment of the invention.
Figure 7:
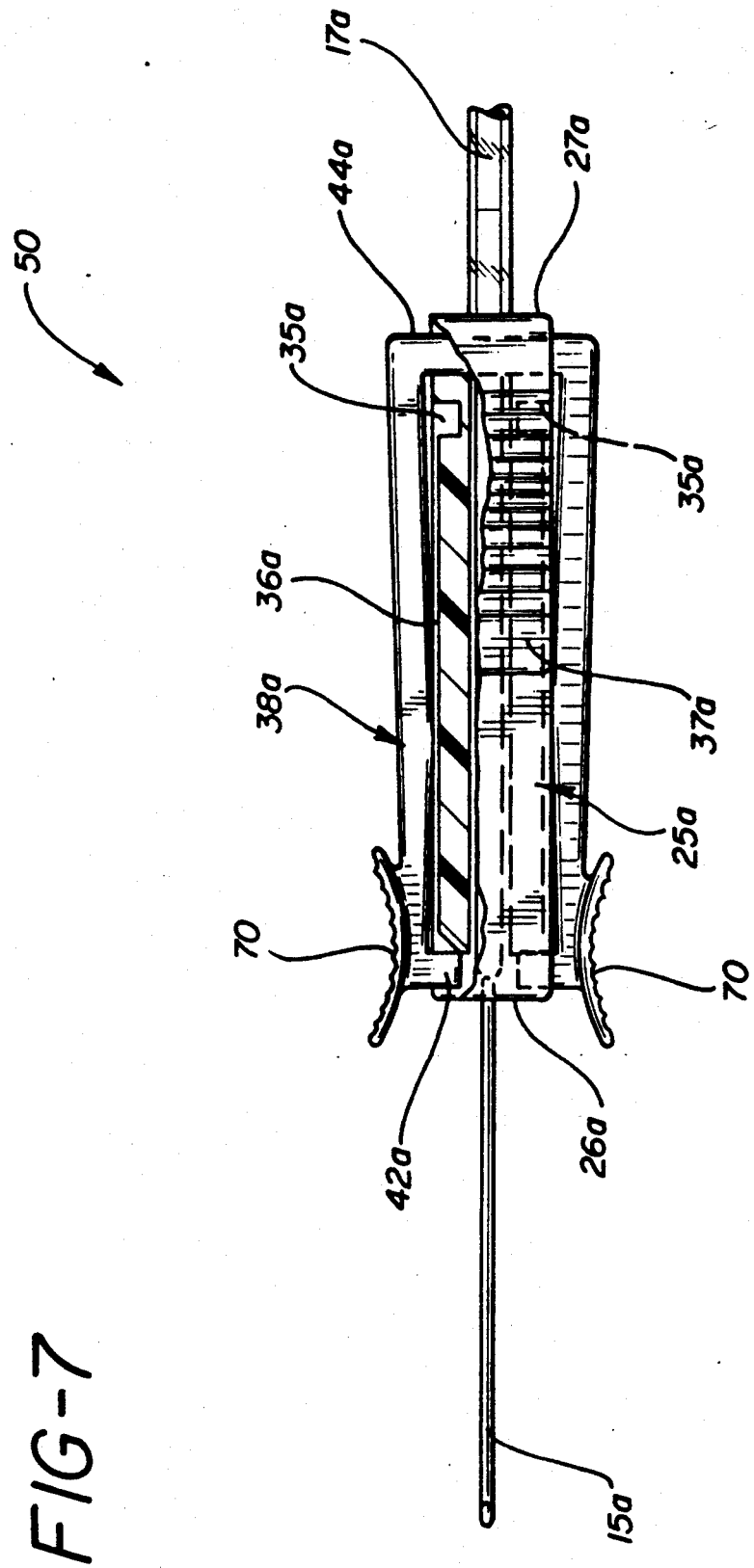
FIG. 7 is a top plan view in partial cross section of the assembly of FIG. 6.

FIGS. 6 and 7, show an additional embodiment of the invention, 50 illustrating a modified assembly wherein wings 70 are located on the housing instead of the needle body.

Wings 70 are attached to the forward end of the outer sides of the housing. Wings 70 are used in the same way as flexible wings on a conventional IV infusion assembly and may be flexible or rigid. Wings 70 provide better gripping means so that needle placement is easier. Furthermore, due to the wings close location relative to the needle tip, the angle of penetration of the needle is improved.

The use of these IV infusion assemblies with a protective cover is no different than the use of a standard butterfly type IV infuser. The assembly is connected to an IV apparatus and the needle placed in the patient. When it is time to remove the needle, the assembly is removed in the same manner as a standard butterfly type IV infuser. Then, the cover is pushed forward by placing the thumb in a position to engage the push projection and to push the cover axially forward to a fully extended position securely covering the used needle. This single hand operation leaves the technician's other hand free to apply pressure in the area of the venipuncture in order to prevent blood flow through the catheter.

The cover and housing are comprised of moldable parts which can be mass produced as will be understood, from a variety of materials including, for example, polyethylene, polyvinyl chloride, polystyrene, certain metals or polypropylene. Materials will be selected which will provide the proper covering and support for the structure of the invention in its use, but which will provide also a degree of resiliency for the purposes of providing the cooperative movement relative to the cooperating abutments of the assembly.

What is claimed is:

1. An IV infusion cover and housing assembly comprising:
   a protective cover comprising a rearward and forward end connected by opposite sidewalls, and a top and bottom side connected to said sidewalls;
   a housing surrounding said cover, said housing comprising a rearward closed end and a forward opened end with protrusions extending into said housing;
   means for advancing said cover out of said housing to a fully extended position; and
   means for locking said cover to said housing in the fully extended position.

2. The assembly of claim 1 further comprising:
   outwardly projecting wings adjacent said forward end of said housing.

3. The assembly of claim 2 wherein said wings are rigid.

4. The assembly of claim 1 wherein said means for advancing said cover comprises a push projection on the top side of said cover.

5. The assembly of claim 1 wherein said cover further comprises cavities in said sidewalls extending between the top side of said cover and the bottom side of said cover, and said cavities engage the protrusions of said housing when said cover is in the fully extended position.

6. An IV infection assembly comprising:
a needle body having a forward and rearward end;
a needle having a distal tip and an elongated shaft terminating in fluid communication with the forward end of said needle body;
a tubing in fluid communication with the rearward end of said needle body;
a protective cover slidably mounted on said tubing, said cover comprising a rearward and forward end connected by opposite sidewalls, a top and bottom side connected to said sidewalls, cavities in said sidewalls extending between the top side and the bottom side, and a push projection on the top side; and
a housing connected to said tubing and surrounding said cover, said housing comprising a rearward closed end, a forward opened end and protrusions extending into said housing.

7. The assembly of claim 6 wherein said cavities of said cover engage the protrusions of said housing when said cover is in a fully extended position.

8. The assembly of claim 7 further comprising:
outwardly projecting wings adjacent said forward end of said housing.

9. The assembly of claim 8 wherein said wings are rigid.

10. The assembly of claim 6 wherein said cover is advanced out of said housing to a fully extended position with said push projection.

11. An IV infusion assembly comprising:
a needle body having a forward and rearward end;
a needle having a distal tip and an elongated shaft terminating in fluid communication with the forward end of said needle body;
a tubing in fluid communication with the rearward end of said needle body;
protective cover slightly mounted on said tubing;
a housing connected to said tubing and surrounding said cover; and
outwardly projecting wings adjacent the forward end of said housing.

12. The assembly of claim 11 further comprising:
means for advancing said cover out of said housing to a fully extended position over said needle.

13. The assembly of claim 12 further comprising:
means for locking said cover to said housing in the fully extended position over said needle.

14. The assembly of claim 12 wherein said cover comprises a rearward and forward end connected by opposite sidewalls, a top and bottom side connected to said sidewalls, and a slot extending from the forward end to the rearward end.

15. The assembly of claim 14 wherein said housing comprises a rearward closed end, a forward opened end and protrusions extending into said housing.

16. The assembly of claim 12 wherein said means for advancing said cover comprises a push projection on said cover.

17. The assembly of claim 15 wherein the protrusions of said housing engage the rearward end of said cover when said cover is in the fully extended position over said needle.

18. The assembly of claim 17 wherein said further comprises cavities which engage with the protrusions of said housing.

19. The assembly of claim 11 wherein said wings are rigid.

* * * * *